United States Patent
Lee et al.

(10) Patent No.: US 11,453,918 B2
(45) Date of Patent: Sep. 27, 2022

(54) METHOD FOR DETECTING LIVE MYCOBACTERIUM TUBERCULOSIS

(71) Applicant: National Tsing Hua University, Hsinchu (TW)

(72) Inventors: Gwo-Bin Lee, Hsinchu (TW); Ka-U Ip, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 287 days.

(21) Appl. No.: 16/152,942

(22) Filed: Oct. 5, 2018

(65) Prior Publication Data

US 2020/0063192 A1  Feb. 27, 2020

(30) Foreign Application Priority Data

Aug. 22, 2018 (TW) ................................ 107129334

(51) Int. Cl.
*C12Q 1/689* (2018.01)
(52) U.S. Cl.
CPC .................................... *C12Q 1/689* (2013.01)
(58) Field of Classification Search
CPC ...................................................... C12Q 1/689
See application file for complete search history.

(56) References Cited

FOREIGN PATENT DOCUMENTS

WO WO-2016085632 A2 * 6/2016 ............. C12Q 1/689

OTHER PUBLICATIONS

Intorasoot, Novel potential diagnostic test for *Mycobacterium tuberculosis* complex using combined immunomagnetic separation (IMS) and PCR-CTPP, J Appl Microbiol, 121(2): 528-538, 2016. (Year: 2016).*
Shin, *Mycobacterium tuberculosis* HBHA Protein Reacts Strongly with the Serum Immunoglobulin M of Tuberculosis Patients, Clin Vaccine Immunol, 13(8): 869-875, 2006. (Year: 2006).*
Xiao, Development of a quantitative real-time PCR assay for viable *Salmonella* spp. without enrichment, Food Control, 57:185-189, 2015. (Year: 2015).*
Lee, An integrated microfluidic system for rapid diagnosis of dengue virus infection, Biosensors and Bioelectronics, 25: 745-752, 2009. (Year: 2009).*
Ka-U Ip et al. "An Integrated Microfluidic System for Identification of Live *Mycobacterium tuberculosis* by Real-Time Polymerase Chain Reaction", 31st International Conference on Micro and Electro Mechanical Systems, Jan. 21-25, 2018.

* cited by examiner

*Primary Examiner* — Angela M. Bertagna
*Assistant Examiner* — Carolyn L Greene
(74) *Attorney, Agent, or Firm* — WPAT, PC (57) ABSTRACT

The present disclosure provides a method for detecting live *Mycobacterium tuberculosis* in a sample. The method of the present disclosure can rapidly detect *Mycobacterium tuberculosis*, identify live *Mycobacterium tuberculosis*, greatly reduce the required reagents and biological samples, and simplify the experimental procedure and time.

5 Claims, 8 Drawing Sheets

□ Live *Mycobacterium tuberculosis* sample ($1.27 \times 10^5$ CFU)
○ Dead *Mycobacterium tuberculosis* sample ($1.27 \times 10^5$ CFU)

METHOD FOR DETECTING LIVE *MYCOBACTERIUM TUBERCULOSIS*

CROSS-REFERENCE TO RELATED APPLICATION

This application claims priority of Taiwan patent application No. 107129334, filed on Aug. 22, 2018, the content of which is incorporated herein in its entirety by reference.

BACKGROUND OF THE INVENTION

1. Field of the Invention

The present invention relates to a method for detecting live *Mycobacterium tuberculosis*.

2. The Prior Art

Tuberculosis (TB) is one of the major infection killers in children and adults, and is the most common infectious disease in the world. At present, one third of the world's population is infected with tuberculosis, of which 20 million are registered cases. It is estimated that tuberculosis will kill 30 million people in the next decade. There are currently more than 50 million people infected with multidrug-resistant (MDR) tuberculosis. The emergence of drug resistance is due to management imbalances in the public health system and lack of proper management of tuberculosis therapies. Before the emergence of multi-drug resistant tuberculosis, the cure rate for multi-drug treatment of tuberculosis is quite high. Nowadays, multidrug-resistant tuberculosis is not only highly infective, but also cannot be completely cured.

Tuberculosis is transmitted by *Mycobacterium tuberculosis*, which is spread by airborne particles and causes irreversible lung damage. If the pathogens are released from the lungs, it may cause systemic diseases, including bones, joints, lungs, spleen, gastrointestinal tract and brain. 50% of people exposed to patients with tuberculosis will be infected, and 15% of those infected will develop the disease. Poverty, malnutrition and overpopulation will increase the spread of tuberculosis. Therefore, how to develop a method and system for detecting *Mycobacterium tuberculosis* is an urgent need for researchers in the field.

The traditional method for detecting *Mycobacterium tuberculosis* is bacterial culture. However, the growth rate of *Mycobacterium tuberculosis* is quite slow, and it takes 6 to 8 weeks or more, making rapid detection more difficult. It takes a long time to use traditional detection methods to obtain the result. In addition, although the rapid screening method such as staining has been developed to detect *Mycobacterium tuberculosis*, the sensitivity of this method is low. If a suspected tuberculosis patient is screened with a negative smear, it is still necessary to wait for bacterial culture and molecular identification results. Furthermore, the detection method cannot distinguish live and dead *Mycobacterium tuberculosis*, and is not suitable for rapid evaluation of prognosis after administration. Therefore, if a rapid method for detecting *Mycobacterium tuberculosis* can be developed, and the method can be used to distinguish live *Mycobacterium tuberculosis*, a considerable breakthrough will be made in the art.

SUMMARY OF THE INVENTION

A primary objective of the present invention is to provide a method for detecting live *Mycobacterium tuberculosis* in a sample, comprising the following steps: (a) coating a plurality of *Mycobacterium tuberculosis*-specific probes on a surface of a plurality of magnetic beads to form a plurality of magnetic bead-probe complexes; (b) mixing the plurality of magnetic bead-probe complexes, a sample from a patient comprising live *Mycobacterium tuberculosis* and dead *Mycobacterium tuberculosis*, and a nucleic acid dye, so that the plurality of magnetic bead-probe complexes and the nucleic acid dye combined with live *Mycobacterium tuberculosis* and dead *Mycobacterium tuberculosis* in the sample; (c) exciting the nucleic acid dye with a blue light; (d) magnetically aspirating the plurality of magnetic bead-probe complexes bound to the live *Mycobacterium tuberculosis* and the dead *Mycobacterium tuberculosis* in the sample with a magnetic field to remove impurities; (e) replacing the magnetic field with a temperature control module, and then performing a DNA amplification reaction on the sample to obtain a reaction product; and (f) combining the reaction product with a fluorescent label to detect a fluorescent signal of the reaction product, wherein the DNA of the dead *Mycobacterium tuberculosis* is not amplified, thereby detecting the live *Mycobacterium tuberculosis* in the sample.

According to an embodiment of the present invention, the sample is isolated from a patient with tuberculosis.

According to an embodiment of the present invention, the fluorescent signal indicates that after the patient with tuberculosis is administered a drug for treating tuberculosis, a ratio of live *Mycobacterium tuberculosis* to dead *Mycobacterium tuberculosis* in the sample is lower than that of live *Mycobacterium tuberculosis* to dead *Mycobacterium tuberculosis* in the sample before administration, representing the drug has a positive effect on killing *Mycobacterium tuberculosis*.

According to an embodiment of the present invention, the nucleic acid dye is propidium monoazide (PMA).

According to an embodiment of the present invention, in the step (d), while the magnetically aspirating is performed, the sample is washed with a washing buffer.

According to an embodiment of the present invention, the DNA amplification reaction is a polymerase chain reaction or a real time quantitative polymerase chain reaction.

According to an embodiment of the present invention, the DNA amplification reaction includes 1 to 30 cycles.

According to an embodiment of the present invention, an operating time of the method ranges from 0.5 to 3.5 hours.

According to an embodiment of the present invention, the method is performed on a microfluidic chip.

According to an embodiment of the present invention, an amount of live *Mycobacterium tuberculosis* detected in the sample ranges from 10 to $10^6$ CFU.

According to an embodiment of the present invention, the plurality of *Mycobacterium tuberculosis*-specific probes bind to an outer membrane of live *Mycobacterium tuberculosis* and dead *Mycobacterium tuberculosis* in the sample.

According to an embodiment of the present invention, each of the plurality of *Mycobacterium tuberculosis*-specific probes binds to a heparin-binding hemagglutinin at the outer membrane.

In summary, the method of the present invention has the effect on rapid detection of *Mycobacterium tuberculosis* and identification of live *Mycobacterium tuberculosis*, greatly reducing the required reagents and biological samples, and the operating time of the method ranges from 0.5 to 3.5 hours, greatly simplifying the experimental process and time. In addition, regarding the evaluation of prognosis after administration, the method of the present invention can more accurately determine the time of the administration, greatly reduce time cost, accurately reduce the drug test, and can reduce the patients' side effects on the drug. Furthermore, the present invention combines live and dead *Mycobacterium tuberculosis* distinguishing technology, and completes separation, purification, mixing, movement and reaction of various reagents, and signal collection in an integrated platform, which is faster and more accurate than the existing methods.

The molecular diagnostic platform of the invention integrates sample pre-treatment, *Mycobacterium tuberculosis* separation, purification, and quantitative analysis into the molecular diagnostic platform. That is, integration of a chip and a platform system can replace a large laboratory and an experienced operator, especially in the handling of *Mycobacterium tuberculosis*, a highly dangerous bacterium, the method of the present invention is more valuable, does not need costly equipment for preventing cross-contamination and spread, and can replace rigorously trained operators.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

As used herein, the term "*Mycobacterium tuberculosis*" means an obligatory aerobic microorganism belonging to the genus *Mycobacterium*.

As used herein, the term "DNA" means a sequence of deoxyribonucleotides in the form of a single or double strand, which may be used interchangeably with the term "gene", "deoxyribonucleic acid" and "nucleic acid molecule".

Example 1

Experimental Procedures of Method for Detecting Live *Mycobacterium tuberculosis* in a Sample of Present Invention The *Mycobacterium tuberculosis* sample used in the present example is *Mycobacterium tuberculosis* H37Ra (obtained from the Institute of Infectious Diseases and Vaccinology, National Health Research Institutes, Taiwan, ATCC 25177) is a non-virulent strain, and has the same phenotype between the virulent and non-virulent forms of *Mycobacterium tuberculosis*.

The method of the present invention can be used in an integrated molecular diagnostic platform for automated operation. The steps of the method generally include purification of *Mycobacterium tuberculosis*, impurity washing, polymerase chain reaction, live and dead bacteria distinction, and quantitative interpretation of results. The experimental procedures of the method are shown in FIG. 1.

Figure 1:
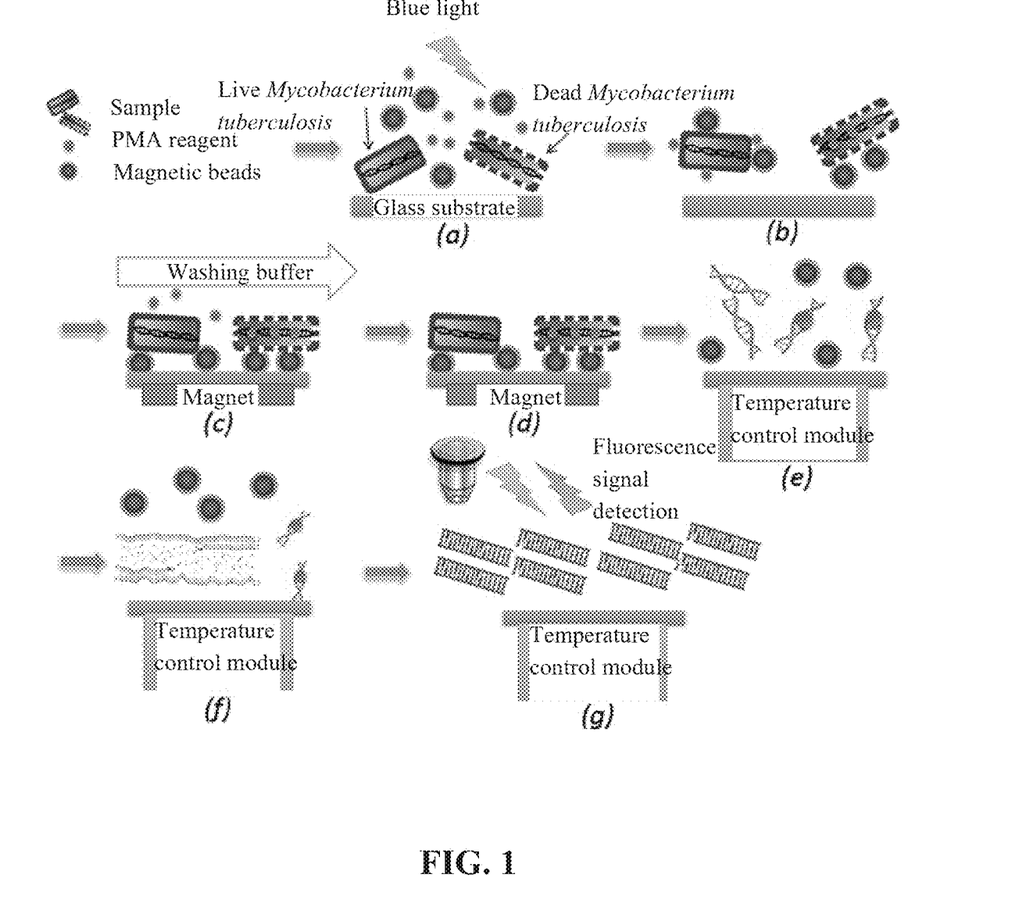
FIG. 1 is a flow chart showing the operation of the method for detecting live *Mycobacterium tuberculosis* in a sample according to an embodiment of the present invention.

As shown in FIG. 1, magnetic beads, a sample comprising live *Mycobacterium tuberculosis* and dead *Mycobacterium tuberculosis*, and propidium monoazide (PMA) were mixed and placed in a sample tank, followed by exciting the PMA into the dead *Mycobacterium tuberculosis* for DNA chimerism using blue light emitting diode (LED) with blue light (HV5-B 1.4A/5V, CHT PRECISION CO., LTD, Taiwan), while the surface of the magnetic beads was coated with *Mycobacterium tuberculosis*-specific probes, which are a modified heparin structure with specific binding heparin-binding hemagglutinin, so that *Mycobacterium tuberculosis* can be specifically captured (see steps (a) and (b)). Subsequently, a magnetic field was used to fix the magnetic beads that have captured the *Mycobacterium tuberculosis* at the bottom, and the sample was washed with a washing buffer (see steps (c) and (d)). The magnetic field was then replaced by a temperature control module (i.e., a polymerase chain reaction reactor), and the polymerase chain reaction reagent was added for real time quantitative polymerase chain reaction (see steps (e) and (f)), wherein the genomic DNA was extracted from the sample and used as a template prior to real time quantitative polymerase chain reaction. The fluorescent signal was detected by the fluorescence detector of the integrated molecular diagnostic platform, quantified into fluorescent quantitative data and displayed on the computer (see step (g)). By the method of the present invention, the dead *Mycobacterium tuberculosis* was unable to be used to perform real time quantitative polymerase chain reaction under PMA, so there was no fluorescent signal. The method can quickly and accurately quantify the amount of *Mycobacterium tuberculosis* after administration, and effectively evaluate the drug effect and prognosis after administration.

Example 2

Method for Detecting Live *Mycobacterium tuberculosis* in a Sample Using a Microfluidic System Comprising a Microfluidic Chip The method of the present invention can be used in an integrated molecular diagnostic platform for automated operation. The integrated molecular diagnostic platform is a microfluidic system comprising a microfluidic chip 1.

Figure 2:
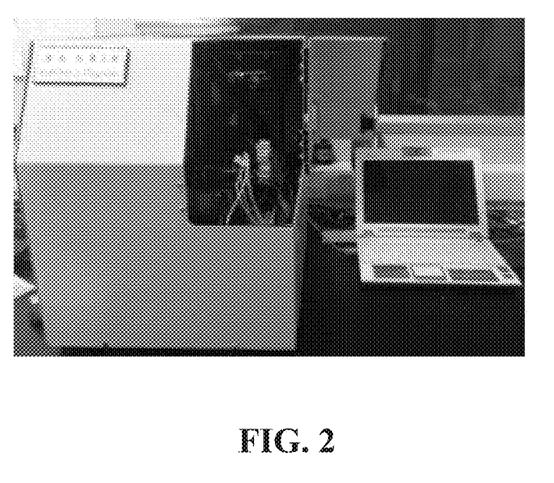
FIG. 2 and FIG. 3 show photographs of the appearance of a microfluidic system.
Figure 3:
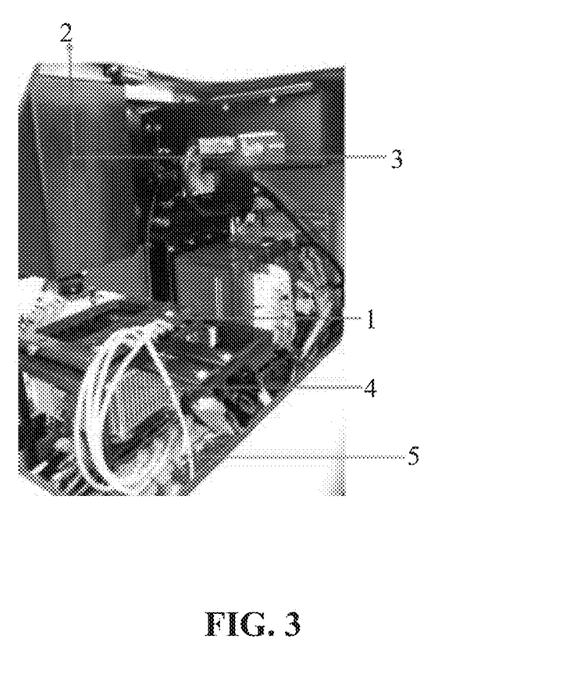

FIG. 2 and FIG. 3 show photographs of the appearance of the microfluidic system. The size of the microfluidic system is 56 cm×38 cm×45 cm. As shown in FIG. 2 and FIG. 3, the microfluidic system is communicatively connected to a notebook to control and display the detection results, and the microfluidic system is equipped with a microfluidic chip 1, a photomultiplier tube (PMT) 2, a laser source 3, a temperature control module 4 and an electromagnetic valve (EMV) 5. Therefore, when the method of the present invention was carried out, it was operated automatically on the integrated molecular diagnostic platform. In addition, real time quantitative polymerase chain reaction was performed in the method of the present invention with $1.77 \times 10^5$ CFU/polymerase chain reaction of *Mycobacterium tuberculosis*, resulting in a Ct value of 17.74. PMT signals of different cycles were also observed, and the result is shown in FIG. 4.

Figure 4:
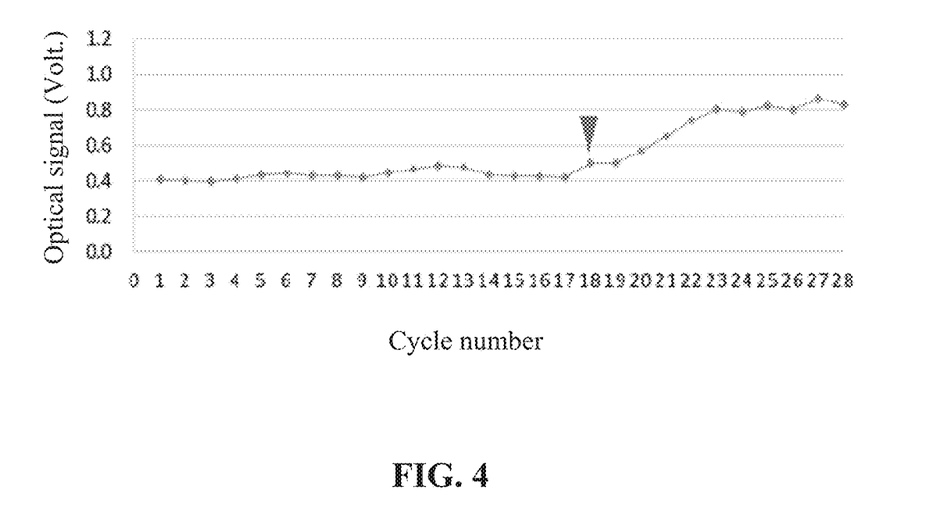
FIG. 4 shows photomultiplier tube (PMT) signals for different cycles of performing real time quantitative polymerase chain reaction.

FIG. 4 shows PMT signals for different cycles of performing real time quantitative polymerase chain reaction. As shown in FIG. 4, there is a significant change in the PMT signal at the 18th cycle number. The result of this example indicates that the method of the present invention can indeed be performed in the microfluidic system.

Example 3

Detection Sensitivity of Method of Present Invention

In this example, a primer set for specifically targeting the genome of *Mycobacterium tuberculosis* was designed according to mycobacterial interspersed repetitive units (MIRU). The forward primer is named ETR-AF, which has the nucleotide sequence of SEQ ID NO: 1. The reverse primer is named ETR-AR, which has the nucleotide sequence of SEQ ID NO: 2. The primer set was used to perform DNA amplification (i.e., real time quantitative polymerase chain reaction) in the method of the present invention. The result of this example is shown in Table 1 and FIG. 5.

TABLE 1

| *Mycobacterium tuberculosis* sample | $Log_{10}$ (CFU) | Ct value |
|---|---|---|
| Negative control | — | 37.11 |
| $1.44 \times 10^6$ CFU | 6.16 | 15.62 |
| $1.44 \times 10^5$ CFU | 5.16 | 19.14 |
| $1.44 \times 10^4$ CFU | 4.16 | 23.09 |
| $1.44 \times 10^3$ CFU | 3.16 | 27.26 |
| $1.44 \times 10^2$ CFU | 2.16 | 31.77 |
| $1.44 \times 10$ CFU | 1.16 | 34.81 |
| 1.44 CFU | 0.16 | 36.23 |

Figure 5:
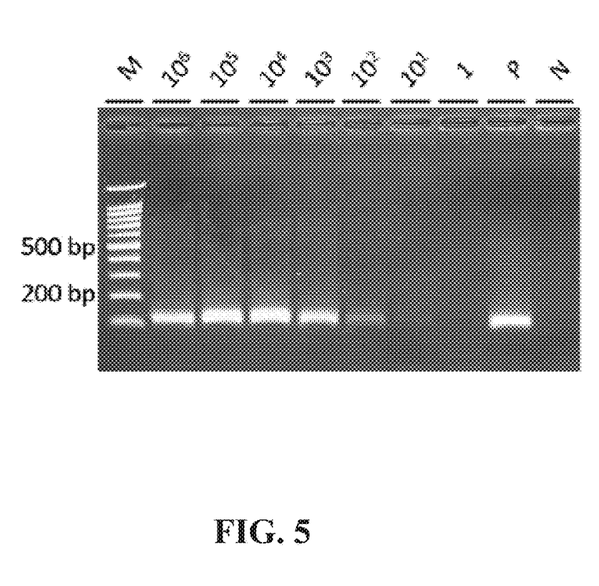
FIG. 5 is an agarose gel electrophoretogram of a PCR product showing the detection sensitivity of the real time quantitative polymerase chain reaction according to the method of the present invention, wherein M represents a marker; P represents a positive control group; and N represents a negative control group.

Table 1 shows the detection sensitivity of real time quantitative polymerase chain reaction according to the method of the present invention. FIG. 5 is an agarose gel electrophoretogram of a PCR product showing the detection sensitivity of the real time quantitative polymerase chain reaction according to the method of the present invention. As shown in Table 1 and FIG. 5, samples with different concentrations of *Mycobacterium tuberculosis* (from 1.44 CFU to $1.44 \times 10^6$ CFU) were subjected to real time quantitative polymerase chain reaction in the method of the present invention, and the limit of detection (LOD) was up to 10-14 CFU/polymerase chain reaction. The result of this example indicates that the method of the present invention has high sensitivity.

Example 4

Method of Present Invention can Effectively Distinguish Live *Mycobacterium tuberculosis*

The conventional detection method of *Mycobacterium tuberculosis* using polymerase chain reaction cannot distinguish live and dead *Mycobacterium tuberculosis*. The detection of *Mycobacterium tuberculosis* was performed according to the procedures of Example 1, and use of 50 μM PMA and activation with light emitting diode (LED) emitting blue light for 15 minutes during the procedures of the method can effectively distinguish live *Mycobacterium tuberculosis*. The result is shown in Table 2 and FIG. 6.

TABLE 2

| | *Mycobacterium tuberculosis* sample | Ct value |
|---|---|---|
| A | Live *Mycobacterium tuberculosis* H37Ra ($1.40 \times 10^6$ CFU) with 50 μM PMA | 16.99 |
| B | Live *Mycobacterium tuberculosis* H37Ra ($1.40 \times 10^6$ CFU) without PMA | 15.58 |
| C | Dead *Mycobacterium tuberculosis* H37Ra ($1.40 \times 10^6$ CFU) with 50 μM PMA | 36.01 |
| D | Dead *Mycobacterium tuberculosis* H37Ra ($1.40 \times 10^6$ CFU) without PMA | 15.45 |
| N | Negative control | 39.18 |

Figure 6:
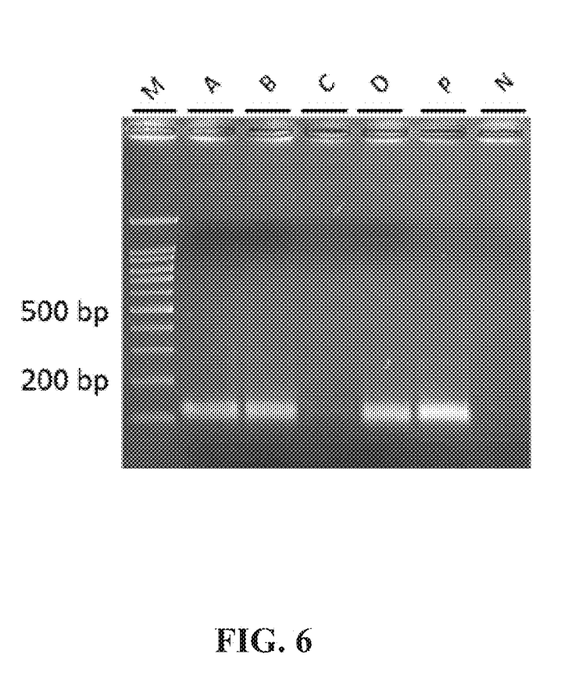
FIG. 6 shows that the method of the present invention can distinguish live *Mycobacterium tuberculosis* using 50 μM PMA, wherein M represents a marker; P represents a positive control group; and N represents a negative control group.

Table 2 and FIG. 6 show that the method of the present invention using 50 μM PMA can distinguish live *Mycobacterium tuberculosis*. As shown in Table 2, when 50 μM PMA was used to treat dead *Mycobacterium tuberculosis* H37Ra, the detected Ct value was close to that of the negative control group. As shown in FIG. 6, when 50 μM PMA was used to treat dead *Mycobacterium tuberculosis* H37Ra, the agarose gel electrophoretogram could not show the signal of the PCR product.

In addition, real time quantitative polymerase chain reaction was performed in the method of the present invention with $1.27 \times 10^5$ CFU live *Mycobacterium tuberculosis* and $1.27 \times 10^5$ CFU dead *Mycobacterium tuberculosis*, and PMT signals of different cycle numbers were observed. The result is shown in FIG. 7.

Figure 7:
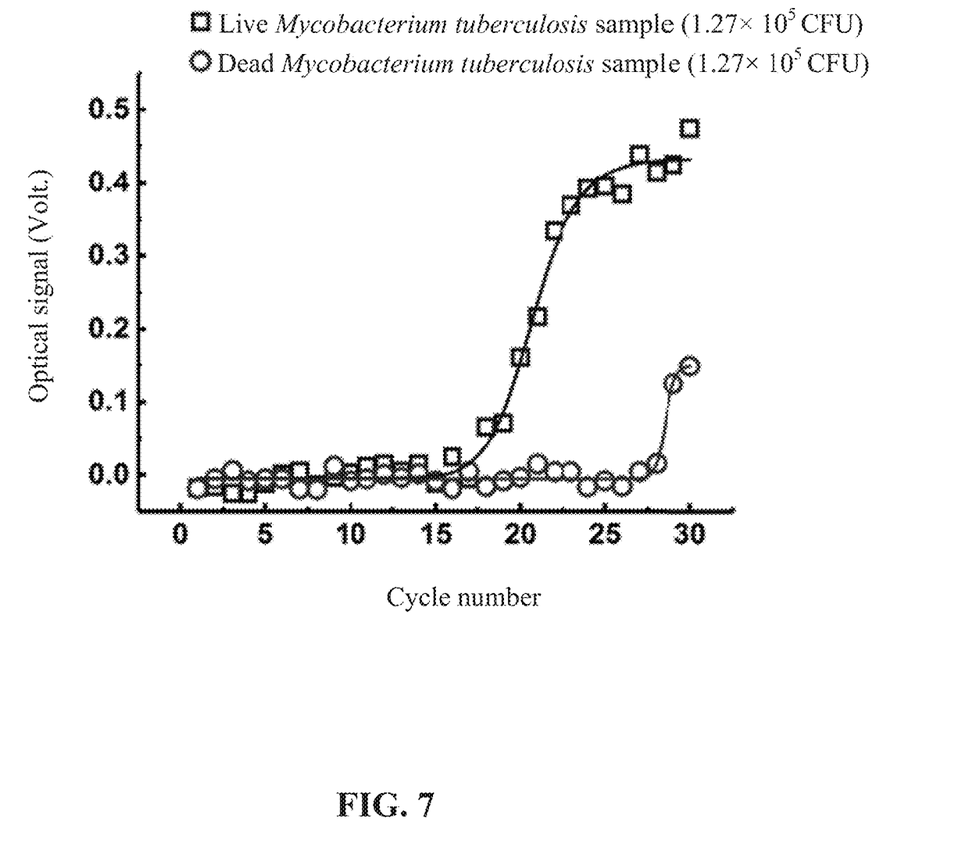
FIG. 7 shows PMT signals for different cycles of performing real time quantitative polymerase chain reaction.

FIG. 7 shows PMT signals for different cycles of performing real time quantitative polymerase chain reaction. As shown in FIG. 7, after the same amount of live and dead *Mycobacterium tuberculosis* samples were treated with PMA, the signals of live *Mycobacterium tuberculosis* samples were produced at the 16th cycle number, and the signals of dead *Mycobacterium tuberculosis* samples were produced at the 29th cycle number.

Real time quantitative polymerase chain reaction was then performed in the method of the present invention with $1.27 \times 10^5$ CFU live *Mycobacterium tuberculosis*, $1.27 \times 10^3$ CFU live *Mycobacterium tuberculosis*, and a mixture comprising $10^5$ CFU dead *Mycobacterium tuberculosis* and $10^3$ CFU live *Mycobacterium tuberculosis*, and PMT signals of different cycle numbers were observed. The result is shown in FIG. 8.

Figure 8:
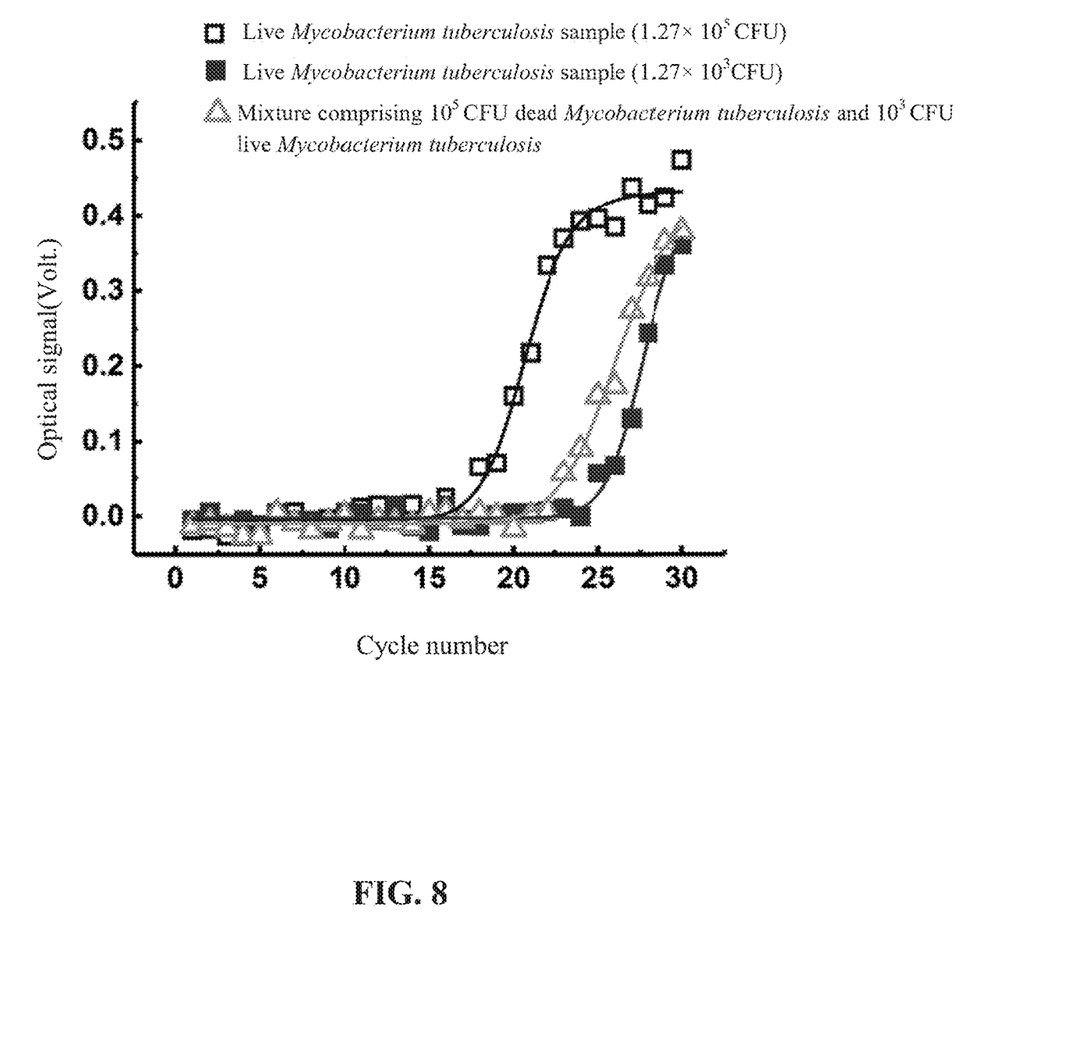
FIG. 8 shows PMT signals for different cycles of performing real time quantitative polymerase chain reaction.

FIG. 8 shows PMT signals for different cycles of performing real time quantitative polymerase chain reaction. As shown in FIG. 8, the PMT signals of the mixture comprising live *Mycobacterium tuberculosis* and dead *Mycobacterium tuberculosis* are similar to the PMT signals of the live *Mycobacterium tuberculosis* sample.

The result of this example indicates that the method of the present invention can detect only live *Mycobacterium tuberculosis* and cannot detect dead *Mycobacterium tuberculosis*, and thus can effectively distinguish live and dead *Mycobacterium tuberculosis*.

In summary, the method of the present invention has the effect on rapid detection of *Mycobacterium tuberculosis* and identification of live *Mycobacterium tuberculosis*, having high sensitivity, greatly reducing the required reagents and biological samples, and the operating time of the method ranges from 0.5 to 3.5 hours, greatly simplifying the experimental process and time. In addition, regarding the evaluation of prognosis after administration, the method of the present invention can more accurately determine the time of the administration, greatly reduce time cost, accurately reduce the drug test, and can reduce the patients' side effects on the drug. Furthermore, the present invention combines live and dead *Mycobacterium tuberculosis* distinguishing technology, and completes separation, purification, mixing, movement and reaction of various reagents, and signal collection in an integrated platform, which is faster and more accurate than the existing methods.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for detecting live *Mycobacterium tuberculosis* H37Ra in a sample, comprising the following steps:
    (a) coating a plurality of *Mycobacterium tuberculosis*-specific probes on a surface of a plurality of magnetic beads to form a plurality of magnetic bead-probe complexes;
    (b) mixing the plurality of magnetic bead-probe complexes, a sample from a patient comprising live *Mycobacterium tuberculosis* H37Ra and dead *Mycobacterium tuberculosis*, and a nucleic acid dye, so that the plurality of magnetic bead-probe complexes and the nucleic acid dye are combined with live *Mycobacterium tuberculosis* H37Ra and dead *Mycobacterium tuberculosis* in the sample;
    (c) exciting the nucleic acid dye with a blue light;
    (d) magnetically aspirating the plurality of magnetic bead-probe complexes bound to the live *Mycobacterium tuberculosis* H37Ra and the dead *Mycobacterium tuberculosis* in the sample with a magnetic field to remove impurities;
    (e) replacing the magnetic field with a temperature control module, and then performing a DNA amplification reaction on the sample to obtain a reaction product; and
    (f) combining the reaction product with a fluorescent label to detect a fluorescent signal of the reaction product, wherein the DNA of the dead *Mycobacterium tuberculosis* is not amplified, thereby detecting the live *Mycobacterium tuberculosis* H37Ra in the sample;
    wherein the plurality of *Mycobacterium tuberculosis*-specific probes bind to an outer membrane of live *Mycobacterium tuberculosis* H37Ra and dead *Mycobacterium tuberculosis* in the sample;
    wherein the steps (a)-(f) of the method are performed in an integrated molecular diagnostic platform comprising a microfluidic chip, a photomultiplier tube (PMT), a laser source, the temperature control module in step (e) and an electromagnetic valve (EMV);
    wherein the nucleic acid dye is propidium monoazide (PMA);
    wherein the DNA amplification reaction is a polymerase chain reaction performed by the temperature control module in step (e); and
    wherein each of the plurality of *Mycobacterium tuberculosis*-specific probes binds to a heparin-binding hemagglutinin at the outer membrane.

2. The method according to claim 1, wherein in the step (d), while the magnetically aspirating is performed, the sample is washed with a washing buffer.

3. The method according to claim 1, wherein the DNA amplification reaction includes 1 to 30 cycles.

4. The method according to claim 1, wherein an operating time of the method ranges from 0.5 to 3.5 hours.

5. The method according to claim 1, wherein an amount of live *Mycobacterium tuberculosis* H37Ra detected in the sample ranges from 10 to $10^6$ CFU.

* * * * *